(12) United States Patent
Ohara et al.

(10) Patent No.: US 7,902,406 B2
(45) Date of Patent: Mar. 8, 2011

(54) LUBRICATING OIL

(75) Inventors: Suguru Ohara, Nagoya (JP); Satoshi Hiyoshi, Yokkaichi (JP); Yukihiro Isogai, Nagoya (JP); Makoto Goto, Yokkaichi (JP)

(73) Assignee: Kyowa Hakko Chemical Co., Ltd., Tokyo (JP)

( * ) Notice: Subject to any disclaimer, the term of this patent is extended or adjusted under 35 U.S.C. 154(b) by 583 days.

(21) Appl. No.: 12/066,300

(22) PCT Filed: Sep. 13, 2006

(86) PCT No.: PCT/JP2006/318149
§ 371 (c)(1),
(2), (4) Date: Mar. 10, 2008

(87) PCT Pub. No.: WO2007/032385
PCT Pub. Date: Mar. 22, 2007

(65) Prior Publication Data
US 2009/0156856 A1    Jun. 18, 2009

(30) Foreign Application Priority Data
Sep. 13, 2005 (JP) .................. 2005-264541

(51) Int. Cl.
*C10M 105/38* (2006.01)
*C07C 31/27* (2006.01)
*C07C 47/347* (2006.01)
*C07C 69/757* (2006.01)
*C10M 169/02* (2006.01)
*C10M 177/00* (2006.01)

(52) U.S. Cl. ........ 568/445; 560/179; 560/190; 568/420; 568/665

(58) Field of Classification Search ................. None
See application file for complete search history.

(56) References Cited

FOREIGN PATENT DOCUMENTS

| JP | 04-159250 | 6/1992 |
|----|-----------|--------|
| JP | 04-339893 | 11/1992 |
| JP | 07-025797 | 1/1995 |
| JP | 2001-064372 | 3/2001 |
| JP | 2001-064374 | 3/2001 |

*Primary Examiner* — Daniel M Sullivan
*Assistant Examiner* — Yevegeny Valenrod
(74) *Attorney, Agent, or Firm* — Fitzpatrick, Cella, Harper & Scinto

(57) ABSTRACT

The present invention provides a lubricating oil comprising an alicyclic compound represented by a general formula (I):

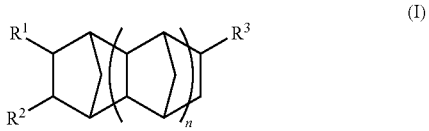

wherein n is an integer of 0 or 1; one of $R^1$ and $R^2$ represents —$CH_2OR^4$ (wherein $R^4$ represents a carboxylic acid residue) while the other one represents alkyl, lower alkyl-substituted or unsubstituted cycloalkyl, aryl, or aralkyl; and $R^3$ represents —$CH_2OR^5$ (wherein $R^5$ represents a carboxylic residue) and the like. The lubricating oil of the present invention has an excellent traction coefficient, excellent heat resistance, or the like. For the lubricating oil of the present invention, the alicyclic compound represented by the general formula (I) can be directly used as it is, and other base oils such as ester oil, poly-α-olefin, mineral oil, or silicone oil may be included therein, if necessary.

5 Claims, No Drawings

LUBRICATING OIL

TECHNICAL FIELD

The present invention relates to a lubricating oil such as an engine oil, an automatic transmission oil, a stepless transmission oil, a gear oil, a power steering oil, a shock absorber oil, a turbine oil, a actuation oil, a refrigeration oil, a rolling oil, a bearing oil, grease, and a lubricating oil for metalworking.

BACKGROUND ART

A compound having norbornane ring and perhydro dimethanonaphthalene ring skeletons is used much in heat resistance resins due to the heat resistance derived from the rigid skeletons thereof. For example, it has been reported that a heat resistance resin hardly giving thermal weight reduction can be obtained by deriving polyester from 2,5-or 2,6-norbornanedimethanol (for example, Patent Document 1).

Meanwhile, it has been demanded for a drive unit of transmission or the like that receives the driving power of an automobile to operate at a higher temperature in accordance with the tendency to increase the output of recent automobiles and miniaturize the unit itself. Especially for a mechanical traction drive unit, heat resistance for the fluid employed therein has particularly been demanded in terms of reduction in weight and manufacturing cost, and high output response.

[Patent Document 1] Japanese Unexamined Patent Publication No. 2001-64374

DISCLOSURE OF THE INVENTION

Problems to be Solved by the Invention

An object of the present invention is to provide a lubricating oil having an excellent traction coefficient, excellent heat resistance, or the like.

Means for Solving the Problems

The present invention provides the following (1) to (5).

(1) A lubricating oil comprising an alicyclic compound represented by a general formula (I):

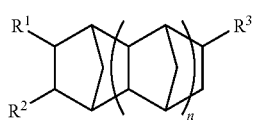

[wherein n is an integer of 0 or 1; one of $R^1$ and $R^2$ represents —$CH_2OR^4$ (where $R^4$ represents a carboxylic acid residue) while the other one represents alkyl, lower alkyl-substituted or unsubstituted cycloalkyl, aryl, or aralkyl; and $R^3$ represents —$CH_2OR^5$ (wherein $R^5$ represents a carboxylic residue)].

(2) A process for producing an alicyclic compound represented by a general formula (I):

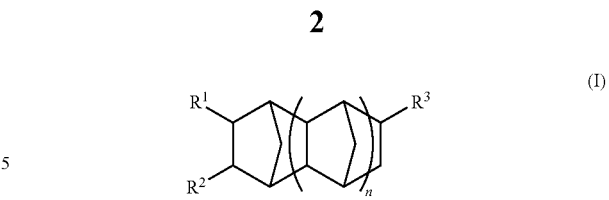

(wherein n, $R^1$, $R^2$, and $R^3$, have the same meaning as defined above, respectively), the process comprising subjecting an alicyclic compound represented by a general formula (II):

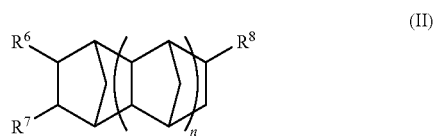

(wherein n is an integer of 0 or 1; one of $R^6$ and $R^7$ represents hydroxymethyl while the other one represents alkyl, lower alkyl-substituted or unsubstituted cycloalkyl, aryl, or aralkyl; and $R^8$ represents hydroxymethyl); to an esterification reaction with carboxylic acid.

(3) An alicyclic compound represented by a general formula (II):

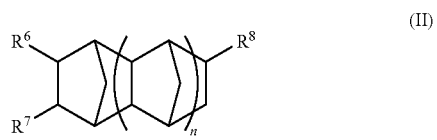

(wherein n, $R^6$, $R^7$, and $R^9$ have the same meaning as defined above, respectively).

(4) A process for producing an alicyclic compound represented by a general formula (I):

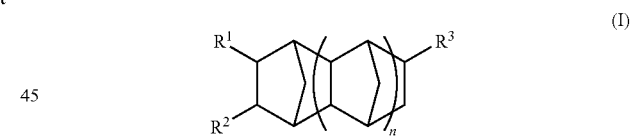

(wherein n, $R^1$, $R^2$, and $R^3$ have the same meaning as defined above, respectively), the process comprising subjecting an alicyclic compound represented by a general formula (IV):

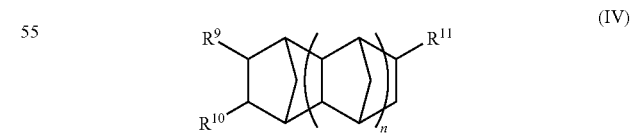

(wherein n has the same meaning as defined above; one of $R^9$ and $R^{10}$ represents formyl while the other one represents alkyl, lower alkyl-substituted or unsubstituted cycloalkyl, aryl, or aralkyl; and $R^{11}$ represents formyl), to a hydrogenation reaction, and further subjecting the thus obtained alicyclic compound represented by a general formula (II):

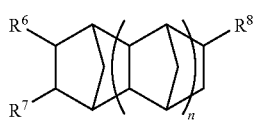

(wherein n, $R^6$, $R^7$, and $R^8$ have the same meaning as defined above, respectively) to an esterification reaction with carboxylic acid.

(5) An alicyclic compound represented by a general formula (IV):

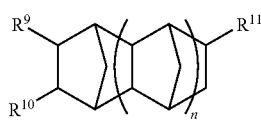

(wherein n, $R^9$, $R^{10}$, and $R^{11}$ have the same meaning as defined above, respectively).

Effect of the Invention

The present invention provides a lubricating oil having an excellent traction coefficient, excellent heat resistance, or the like can be provided.

BEST MODE FOR CARRYING OUT THE INVENTION

For each group defined in the general formulas, examples of the alkyl include linear or branched alkyls having 1 to 18 carbon atom(s), specifically, methyl, ethyl, propyl, isopropyl, butyl, isobutyl, sec-butyl, tert-butyl, pentyl, hexyl, heptyl, octyl, nonyl, decyl, dodecyl, octadecyl, and the like. Among these, preferred are alkyl having 1 to 6 carbon atom(s), and more preferred are alkyl having 1 to 3 carbon atom(s).

Examples of the cycloalkyl include cycloalkyls having 3 to 8 carbon atoms, specifically, cyclopropyl, cyclobutyl, cyclopentyl, cyclohexyl, cycloheptyl, cyclooctyl, and the like.

Examples of the lower alkyl-substituted cycloalkyl include cycloakyl having 3 to 8 carbon atoms which are each substituted with alkyl having 1 to 3 carbon atom(s), specifically, 2-methylcyclohexyl, 3-methylcyclohexyl, 4-methylcyclohexyl, 2,3-dimethylcyclohexyl, 2,4-dimethylcyclohexyl, 2,5-dimethylcyclohexyl, 2-methylcyclohexylmethyl, 3-methylcyclohexylmethyl, 4-methylcyclohexylmethyl, and the like.

Examples of the aryl include aryls having 6 to 14 carbon atoms, specifically, phenyl, naphthyl, and the like.

Examples of the aralkyl include aralkyl having 7 to 15 carbon atoms, specifically, benzyl, phenethyl, naphthylmethyl, naphthylethyl, and the like.

Examples of carboxylic acid in the carboxylic residue and the carboxylic acid include preferably isobutyric acid, cyclopentanecarboxylic acid, cyclohexanecarboxylic acid, methylcyclohexanecarboxylic acid, 2-methylhexanoic acid, cyclooctanecarboxylic acid, 3,5,5-trimethylhexanoic acid, pivalic acid, Versatec 10 (registered trademark, manufactured by Japan Epoxy Resins Co., Ltd.), succinic acid, glutaric acid, 2,4-dimethylglutaric acid, adipic acid, sebacic acid, dodecanedioic acid, phthalic acids, hydrogenated phthalic acids, naphthalene diacid, cyclohexanedicarboxylic acid, norbornane diacid, hymic acid, tricyclodecane dicarboxylic acid, trimellitic acid, pyromelitic acid, and the like. Among these, preferred is cyclohexanecarboxylic acid.

For the alicyclic compound represented by the general formula (II), preferred is a compound in which one of $R^6$ and $R^7$ is hydroxymethyl while the other one is alkyl.

For the alicyclic compound represented by the general formula (IV), preferred is a compound in which one of $R^9$ and $R^{10}$ is formyl while the other one is alkyl.

The alicyclic compound represented by a general formula (IV):

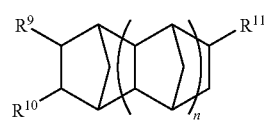

(wherein n, $R^9$, $R^{10}$, and $R^{11}$ have the same meaning as defined above, respectively) can be produced by carrying out in the presence of a suitable catalyst a hydroformylation reaction of an alicyclic compound represented by a general formula (III):

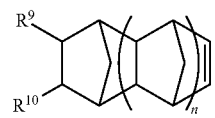

(wherein n, $R^9$, and $R^{10}$ have the same meaning as defined above, respectively).

The alicyclic compound represented by the general formula (III) such as 2-formyl-3-substituted-5-norbornene in which n is 0 and 2-formyl-3-substituted-1,2,3,4,4a,5,8,8a-octahydro-1,4:5,8-dimethanonaphthalene in which n is 1 can be produced, respectively, from a cyclopentadiene derivative and α,β-unsaturated aldehydes in accordance with a well known method [for example, Ann. Vol. 470, page 62 (1929), or the like].

For the conditions for subjecting the alicyclic compound represented by the general formula (III) to a hydroformylation reaction, a catalyst normally used in a hydroformylation reaction, for example, a cobalt catalyst, a well-known noble metal catalyst such as a rhodium catalyst or a platinum catalyst, or the like can be used. Among these, a cobalt catalyst is preferred from the viewpoint of catalyst recovery and a rhodium catalyst is preferred from the viewpoints of reactivity and reaction selectivity. As the catalyst compound, a metal carbonyl complex compound or an arbitrary compound capable of forming a metal carbonyl complex compound in the reaction system can be used. In addition, these catalyst compounds each supported on a suitable carrier, such as a compound supported on silica gel, activated carbon, or the like, can also be used as the catalyst. Specific examples of such catalyst include oxides of the metals, various carboxylate salts such as acetylacetonate salt, chlorides, triphenylphosphine complex, and the like. More specifically, $CO_2(CO)_8$, $CO_4(CO)_{12}$, $CO_6(CO)_{16}$, $HCo(CO)_4$, $[Co(CO)_3(C_5H_5)]_2$ (in the formula, $C_5H_6$ represents cyclopentadienyl), $Rh_4(CO)_{12}$, $Rh_6(CO)_{16}$, $RhCl(PPh_3)_3$, $[RhCl(CO)_2]_2$, $HRh(CO)(PPh_3)_3$ (in the formula, Ph represents phenyl, and same applies below), $Rh(CO)_2(acac)$ (in the formula, acac represents an acetylacetonate group), $Rh(CO)(PPh_3)(acac)$, and the like can be preferably used. These catalysts may be either used alone or in combination of two or more kinds thereof.

For a suitable catalyst concentration, the concentration of catalytic metal (for example, rhodium, cobalt, or the like) is in the range of 5 to 5,000 ppm, more preferably 10 to 2,000 ppm, with respect to the substrate.

In addition, coexistence of a trisubstituted phosphorous compound preferably coexists in an amount excessive with respect to the catalyst, is preferred from the viewpoints of catalyst life and reaction selectivity.

Examples of the trisubstituted phosphorous compound include trisubstituted phosphine such as tributyl phosphine, tri-2-ethylhexylphosphine, tricyclopropyl phosphine, tricyclohexyl phosphine, triphenyl phosphine, tritolyl phosphine, and tris(2-methylphenyl)phosphine; trisubstituted phosphite such as diphenylisodecyl phosphite, phenyldiisodecyl phosphite, tris(nonylphenyl)phosphite, tris(2-tert-butylphenyl)phosphite, tris(2,4-di-tert-butylphenyl)phosphite, tris(2-methylphenyl)phosphite, tris(3-methyl-6-tert-butylphenyl)phosphite, and tris(3-methoxy-6-tert-butylphenyl)phosphite; and water soluble phosphines such as metal salts of diphenylphosphinobenzene-3-sulfonate and metal salts of triphenylphosphinetrisulfonate. These phosphorous compounds may be either used alone or in combination of two or more kinds thereof.

The amount of these trisubstituted phosphorous compounds used is in the range of preferably 1 to 500 times by mole, preferably 3 to 300 times by mole, based on the metal (rhodium, cobalt, or the like).

The hydroformylation reaction can be more suitably carried out by using an organic solvent inert to the reaction. Specific examples of such solvent include alcohol such as ethanol and butanol; saturated aliphatic hydrocarbon such as pentane, hexane, heptane, octane, isooctane, decane, dodecane, and tetradecane; alicyclic hydrocarbon such as cyclohexane, methylcyclohexane, dimethylcyclohexane, cyclooctane, cyclododecane, and decaline; aromatic hydrocarbon such as benzene, toluene, xylene, and alkylnaphthalene; ethers such as dibutylether, methyl tert-butylether, and tetrahydrofuran; nitrile such as acetonitrile and propionitrile; and the like. These reaction solvents may be either used alone or in combination of two or more kinds thereof.

The reaction temperature of the hydroformylation reaction is preferably from 40 to 160° C., and more preferably from 70 to 140° C. The reaction pressure is preferably set between 1 and 20 MPa. In addition, as a gas composition, the molar ratio of carbon monoxide to hydrogen (carbon monoxide/hydrogen) can be arbitrarily selected from the range of 5 to 0.2. Further, a gas inert to the hydroformylation reaction, for example, methane, ethane, propane, nitrogen, helium, argon, carbon dioxide, or the like, may also coexist in the reaction system.

The reaction time required for the hydroformylation reaction varies depending on the reaction temperature, catalyst concentration, concentration of the alicyclic compound represented by the general formula (III) serving as a raw compound, reaction pressure, form of vessel to be used, and the like, but is usually in the range of 10 minutes to 50 hours.

The hydroformylation reaction can be carried out continuously or batch-wisely in any of a stirring-type reaction vessel, a tower-type reaction vessel, and a tube-type reaction vessel.

After completion of the hydroformylation reaction, the alicyclic compound represented by the general formula (IV), which is a product, is separated from the reaction mixture by a usual isolating operation. The alicyclic compound in which n in the general formula (IV) is 0 can be purified by a distillation operation as long as it is carried out under high vacuum conditions. Meanwhile, the alicyclic compound in which n in the general formula (IV) is 1 is more preferably purified by means of recrystallization, extraction, or the like.

The alicyclic compound represented by the general formula (II) can be produced by reducing the alicyclic compound represented by the general formula (IV) that is obtained from the above-mentioned hydroformylation reaction. The reducing process may be carried out at any time before or after separating the hydroformylation product. The reduction reaction can be carried out using a reducing reagent that generates hydride such as sodium borohydride, but industrially, it is advantageous to carry out with hydrogen gas in the presence of a catalyst.

For the reduction with the hydrogen gas, a well-known arbitrarily catalyst which can be used in hydrogenation of an aldehyde compound can be used. Specific examples thereof preferably include Raney nickel, Raney cobalt, nickel diatomaceous earth, copper-chromium catalysts, and catalysts in which palladium, platinum, rhodium, ruthenium, or the like which is supported on silica gel, alumina, or the like.

The catalyst concentration is preferably in the range of usually 0.001 to 10 weight % based on the reaction mixture.

The reduction reaction can be suitably carried out by selecting an appropriate solvent. Specific examples of the solvent include water, alcohol such as water, ethanol, and butanol, and water-containing alcohol; esters such as methyl acetate and ethyl acetate; saturated aliphatic hydrocarbon such as pentane, hexane, heptane, octane, decane, and dodecane; aromatic hydrocarbons such as benzene, toluene, xylene, and alkylnaphthalene; and ether such as tetrahydrofuran and dioxane. These reaction solvents may be either used alone or in combination of two or more kinds thereof.

The temperature for the reduction varies reaction depending on the catalyst to be used and reaction conditions. However, when the temperature is in the range of usually 30 to 250° C., more preferably 50 to 200° C., it offers advantages in reaction rate, catalyst stability, and the like.

The pressure for the reaction varies depending on the catalyst to be used and reaction conditions, but can be selected from pressures of usually 1 to 300 MPa, more preferably 3 to 200 MPa. In addition, a gas inert to the reduction, such as methane, ethane, propane, nitrogen, helium, argon, or carbon dioxide, may coexist in the reaction system.

The reduction can be carried out continuously or batch-wisely in any of a stirring-type reaction vessel, a tower-type reaction vessel, and a tube-type reaction vessel.

After completion of the reduction, the product is isolated by a method such as distillation, recrystallization, or extraction.

The alicyclic compound represented by the general formula (II) can be subjected to an esterification reaction with carboxylic acid to give the alicyclic compound represented by the general formula (I).

The alicyclic compound represented by the general formula (I) can be obtained by subjecting the alicyclic compound represented by the general formula (II) to a reaction with preferably 1 to 10 equivalent, more preferably 1 to 3 equivalent amount of any carboxylic acid, in the presence of an azeotropic agent as necessary, and in the presence of an esterification reaction catalyst (p-toluenesulfonate, etc.) in an catalyst amount to 0.5 equivalent, at a temperature between 50 and 180° C. Examples of the azeotropic agent include toluene, benzene, and the like, and the agent may be used in an amount of usually 0.5 to 100 equivalent, based on the alicyclic compound represented by the general formula (II). As the carboxylic acid, the same carboxylic acids mentioned before can be exemplified.

For the lubricating oil of the invention, the alicyclic compound represented by the general formula (I) can be directly used, but if necessary, other base oils such as ester oil, poly-α-olefin, mineral oil, and silicone oil may be included.

Examples of the ester oil include a monoester of fatty acid, a diester of adipic acid, a diester of pimelic acid, a diester of suberic acid, a diester of azelaic acid, a diester of sebacic acid, a diester of phthalic acid, polyol polyester, and the like.

Examples of the mineral oil include paraffin-base crude oil, intermediate-base crude oil, naphthene-base crude oil, and the like.

The amount of other base oils to be used is not particularly limited, but is preferably 90 weight % or less, more preferably 50 weight % or less, to the alicyclic compound represented by the general formula (I).

The lubricating oil of the invention can also be obtained by, if necessary, adding an additive such as a detergent/dispersant, an antioxidant, an extreme pressure agent, a friction modifier, an oily agent, an antirust agent, a vapor-phase inhibitor, a pour-point depressant, a viscosity improver, an antiseptic agent, an antifoam, a demulsifier, an extreme pressure additive, dye, and flavor. The amount of such additive to be added in the lubricating oil of the invention is not particularly limited, but is preferably from 0.001 to 5 weight %.

Examples of the lubricating oil include an engine oil, an automatic transmission oil, a stepless transmission oil, a gear oil, a power steering oil, a shock absorber oil, a turbine oil, a actuation oil, a refrigeration oil, a rolling oil, a bearing oil, grease, and a lubricating oil for metalworking, and the like.

The engine oil is a lubricating oil used for lubrication of sliding parts of a piston ring and a cylinder, con rod and crankshaft bearings, valve operating system of cam and valve lifter, and the like, in four cycle gasoline engines, two cycle gasoline engines, and diesel engines such as automobiles, motorcycles, motor bikes, trains, ships, submarines, and planes.

The automatic transmission oil is a lubricating oil used for lubrication of various gears, wear adjustment, and power transmission of an automatic transmission including a fluid transmission, a gear device, a wet clutch, and a hydraulic mechanism controlling the same.

The stepless transmission oil is a lubricating oil used for stepless transmission. The stepless transmission oil divides into a belt-drive type and a traction-drive type, and can be used as transmission for automobiles, machine tools, industrial machines, and the like. The belt-drive type stepless transmission comprises two pulleys, one on the engine side and the other one on the driving wheel side, and a belt placed therebetween. The lubricating oil is used in hydraulic actuation and lubrication of a belt part, a clutch plate, and a hydraulic system. The traction-drive type stepless transmission is for transmitting torque by rollers via an oil film, and the lubricating oil is used for transmitting the torque and preventing rollers from burning or wearing. Benefits of the fluid of the invention are not particularly limited to the traction-drive type stepless transmission and can also be applied to the belt-drive type stepless transmission.

The power steering oil is a lubricating oil used in a power steering device for the purpose of reducing the force applied on a handle.

The shock absorber oil is a lubricating oil used for shock absorber in a suspension device for the purpose of providing steering stability of an automobile as well as riding comfort, or is a lubricating oil used for shock absorber for preventing vibration in devices that generate various variations such as a pulverizer.

The turbine oil is a lubricating oil used for lubrication of turbine bearing and reduction gear, and can be used in steam turbines, gas turbines, atomic turbines, and the like, of an electric power generator, a ship, and a plane.

The actuation oil is a lubricating oil used for lubrication of sliding parts and power transmission of hydraulic machinery and devices, and can be used in hydraulic machinery and devices such as construction machines, tool machineries, processing machines for metals and plastics, vehicles, ships, and planes.

The refrigeration oil is a lubricating oil used by being brought into contact with and being coexisted with coolant in a compressor of refrigerators. The refrigeration oil can be used in an air conditioner, a refrigerator, and a freezer for freezing and refrigerating for processing and distribution of food and for industrial use.

The rolling oil is a lubricating oil used for the purpose of providing lubricity on a site of friction caused between a material and rollers upon rolling a metallic material such as iron and steel and an aluminum alloy.

The bearing oil is a lubricating oil used in electronic devices equipped with a driving motor, such as a hard disc, a convection fan, a mobile phone, a laser printer, a digital copying machine, a laser plate maker, a measuring instrument, and a bar code reader; devices essentially equipped with a rotating equipment such as replying, video-recording, audio-recording, and recording devices, examples including a magnetic disc, an optical disk, a floppy disk, a mini-disc, a compact disk, a laser disc, DVD, a blue-ray disc, a digital video, and a video tape; household appliances equipped with a driving motor, such as a refrigerator, a microwave, a vacuum cleaner, a washing machine, a dryer, an electric fan, an air conditioner, and a shaver; precision instruments equipped with a driving unit, such as a clock, a camera, an electric power generator for turbines, a compressor, a micromachine, a robot, a radar, an artificial satellite, and a space station; tools equipped with a driving motor, such as a remote control and a radio control; transport machines, such as an automobile, a train, a ship, a submarine, a plane, and a rocket; and medical instruments equipped with a driving motor, such as a pump for an artificial heart and lung, a pump for dialysis, a hand piece, a bed for medical use, a care nursing bed, an electric wheelchair, and a massage chair.

The grease is in a semi-solid or solid form made by dispersing a thickener in a lubricating oil. For automobiles, the grease is used in a wheel bearing, a constant velocity ball joint, a universal joint, a propeller shaft center support, a clutch release bearing, a water pump bearing, linkage mechanism parts of steering or an accelerator, bearings of electrical components and the like, a spline part of a propeller shaft, a wire cable part for instrumentation, body parts such as a wind regulator and side mirrors, and parts for a brake. For industrial use, the grease is used in machines equipped with sliding and rolling bearings, joints such as gear and chains, machinery sliding faces, or the like.

The lubricating oil for metalworking is a lubricating oil used for lubrication and cooling upon metal machine working. Types of such oil include cutting oil, rolling oil, lubricating oil for press working, drawing oil, and the like.

The lubricating oils thus obtained are expected to exhibit excellent heat resistance, an excellent traction coefficient, or an excellent viscosity index, as well as high performance on solubility with respect to various additives, a traction coefficient at high temperature, or oxidation stability.

Hereinafter, the invention will be described with reference to Examples, but the invention is not limited to these Examples.

The measurement data in Examples and Test Examples were obtained by the following measurement instruments and measurement procedures:

Infrared spectroscopy spectra (IR): FTS-40A (manufactured by Japan Bio-Rad)

Nuclear magnetic resonance spectrum ($^1$H-NMR, $^{13}$C-NMR: tetramethylsilane was used as a reference): GSX-400 (400 MHz) (manufactured by JEOL)

Kinetic Viscosity: measurement was carried out using a Cannon-Fenske viscometer in accordance with a normal method (JIS K2283) under a temperature condition of 40° C.

EXAMPLE 1

(Process 1)

Into a stainless electromagnetic stirring-type autoclave having an internal volume of 1 liter, 136 g of 2-formyl-3-methyl-5-norbornene prepared from cyclopentadiene and crotonaldehyde, 200 ml of methylcyclohexane, 12 mg of Rh(CO)(PPh$_3$)(acac), and 655 mg of triphenylphosphine were charged. The system was thoroughly purged with a mixed gas of carbon monoxide and hydrogen in a molar ratio of 1/1, and then the mixture was heated under stirring and the temperature inside the system was raised to 120° C. in about 30 minutes while maintaining the pressure inside the system at 4 MPa with the gas. The mixture was further stirred for 4 hours while still maintaining the temperature inside the system at 120° C. During the reaction, a mixed gas of carbon monoxide and hydrogen in a molar ratio of 1/1 was successively supplied via a pressure-control valve so as to always maintain the pressure of the autoclave at 5 MPa.

After the reaction, the reaction mixture was taken out from the autoclave, and the methylcyclohexane was concentrated and removed. The thus obtained residue was subjected to distillation under reduced pressure, and as a result, 167 g of distillate of the present process was obtained. This distillate was analyzed by FT-IR and $^1$H NMR, and as a result, it was confirmed that it is 2,5(6)-diformyl-3-methylnorbornene.

$^1$H-NMR (CDCl$_3$, δppm): 0.99-1.59 (m, 6H), 1.76-3.02 (m, 6H), 9.56-9.88 (m, 2H)

FT-IR (KBr, Neat; cm$^{-1}$): 2958, 2875, 2817, 1714, 1727, 1457

(Process 2)

Into a stainless electromagnetic stirring-type autoclave having an internal volume of 1 liter, 167 g of the distillate containing 2,5(6)-diformyl-3-methylnorbornene obtained in Process 1, 334 g of ethanol, and 25 g of a Raney nickel catalyst were charged. The system was thoroughly purged with hydrogen gas, and then the mixture was heated under stirring and the temperature inside the system was raised to 100° C. in about 30 minutes while maintaining the pressure inside the system at 5 MPa with the gas. The mixture was further stirred for 2 hours while still maintaining the temperature inside the system at 100° C. During the reaction, hydrogen gas was successively supplied via a pressure-control valve so as to always maintain the pressure of the autoclave at 5 MPa.

After the reaction, the reaction mixture was taken out from the autoclave, the catalyst was filtered, and the ethanol was concentrated and removed. The thus obtained mixed solution was subjected to distillation under reduced pressure, and as a result, 155 g of distillate of the present process was obtained. This distillate was analyzed by FT-IR and $^1$H NMR, and as a result, it was confirmed that it is 2,5(6)-bishydroxymethyl-3-methylnorbornene.

$^1$H-NMR (CDCl$_3$, δppm): 0.78-1.14 (m, 5H), 1.20-1.49 (m, 3H), 1.50-1.83 (m, 2H), 1.89-2.34 (m, 2H), 2.48-3.18 (br, 2H), 3.27-3.68 (m, 4H)

FT-IR (KBr, Neat; cm$^{-1}$): 3332, 2949, 2869, 1455, 1375, 1037, 647

(Process 3)

85 g of 2,5(6)-bishydroxymethyl-3-methylnorbornene obtained in Process 2 and 192 g of cyclohexanecarboxylic acid were charged into a reaction flask. The mixture was thoroughly stirred under nitrogen substitution, and then kept at 180° C. for 1 hour and subsequently heated to 210° C. for a reaction to take place for 8 hours. After the reaction, the reaction mixture was cooled to room temperature, and the unreacted acid component was distilled off under reduced pressure at 150° C. Next, the reaction solution was neutralized with a saturated aqueous solution of sodium bicarbonate, washed with water, and the water content was removed under reduced pressure at 130° C., to obtain 173 g of an alicyclic compound.

$^1$H-NMR (CDCl$_3$, δppm): 0.84-2.32 (m, 34H), 3.76-4.14 (m, 4H)

FT-IR (KBr, Neat; cm$^{-1}$): 2934, 2856, 1732, 1451, 1246, 1169

COMPARATIVE EXAMPLE 1

(Process 1)

The reaction was carried out in the same manner as in Process 1 of Example 1, except that 122 g of 2-formyl-5-norbornene was used instead of 136 g of 2-formyl-3-methyl-5-norbornane. After the reaction, 152 g of a mixed reaction product was obtained in accordance with the same procedures as in Process 1 of Example 1.

(Process 2)

Into a stainless electromagnetic stirring-type autoclave having an internal volume of 1 liter, 152 g of the mixed reaction solution obtained in Process 1, 304 g of ethanol, and 23 g of a Raney nickel catalyst were charged. The reaction was carried out under the same conditions as in Process 2 of Example 1. After the reaction, the reaction mixed solution was taken out from the autoclave, the catalyst was filtered, and the ethanol was concentrated and removed. The thus obtained mixed solution was subjected to distillation under reduced pressure, and as a result, 137 g of 2,5(6)-bishydroxymethylnorbornane was obtained as a distillate of the present process.

(Process 3)

137 g of 2,5(6)-bishydroxymethylnorbornane obtained in Process 2 and 337 g of cyclohexanecarboxylic acid were charged into a reaction flask, and the reaction was carried out under the same conditions as in Process 3 of Example 1. After the reaction, the reaction mixture was cooled to room temperature, and then the unreacted acid component was distilled off under reduced pressure at 150° C. Next, the reaction solution was neutralized with a saturated aqueous solution of sodium bicarbonate, washed with water, and the water content was removed under reduced pressure at 130° C., to obtain 300 g of an ester compound.

COMPARATIVE EXAMPLE 2

33 g of 12-tungstophosphoric acid was added to 300 g of α-methylstyrene, and the mixture was heated for 5 minutes at 130° C. and stirred for a dimerization reaction to take place. Then, the reaction mixture was cooled in a water bath at 20° C. and the solid catalyst was removed by filtration. To the thus obtained filtrate, 15 g of palladium carbon (10 weight % of palladium content) and 3 L of cyclohexane were added, a hydrogenation reaction was carried out at 180° C. under a hydrogen pressure of 40 kg/cm² in gauge pressure for 6 hours, to obtain 300 g of 2,4-dicyclohexyl-2-methylpentane which is the hydride of α-methylstyrene dimer containing linear units in a proportion of 96 weight %.

TEST EXAMPLE 1

(Measurement of Traction Coefficient)
Compounds obtained in Example 1, Comparative Example 1, and Comparative Example 2, and 'SANTOTRAC 50' produced by Nippon Oil Corporation were each subjected to a measurement of traction coefficient with the use of a four-cylinder type traction tester. The results are shown in Table 1.

TEST EXAMPLE 2

(Determination of Heat Resistance)
The alicyclic compound obtained in Example 1 and SANTOTRAC were each subjected to measurement to give a DTA curve using a Differential Thermal Analyzer (DTA). Then, temperatures where the weight ratio had been decreased by 5%, 10%, and 50% as compared to that before the test were compared. The results are shown in Table 2.

TABLE 1

Measurement Values of Fluids and Traction Coefficients

|  | Example 1 | Comparative Example 1 | Comparative Example 2 | SANTOTRAC 50 |
|---|---|---|---|---|
| Oil Temperature (° C.) | 40 | 38 | 40 | 41 |
| Viscosity Index | 39 | 40 | 7 | 123 |
| Kinetic Viscosity at 40° C. (cSt) | 242 | 236 | 20 | 30 |
| Traction Coefficient | 0.1025 | 0.0984 | 0.0982 | 0.1025 |

TABLE 2

Reduction in Weight of Fluids and Temperatures

|  | Example 1 | SANTOTRAC 50 |
|---|---|---|
| −5% (° C.) | 239 | 146 |
| −10% (° C.) | 255 | 161 |
| −50% (° C.) | 297 | 197 |

According to Tables 1 and 2, the alicyclic compound obtained in Example 1 was excellent in the points of traction coefficient or heat resistance as compared to that of the compounds obtained in Comparative Examples 1 and 2, and SANTOTRAC 50.

As above, it was found that the alicyclic compound obtained in Example 1 is useful as a lubricating oil having an excellent traction coefficient and excellent heat resistance.

INDUSTRIAL APPLICABILITY

According to the present invention, a lubricating oil having an excellent traction coefficient, excellent heat resistance, or the like can be provided.

The invention claimed is:
1. A lubricating oil comprising an alicyclic compound represented by formula (I):

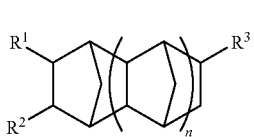

wherein n is an integer of 0 or 1;
one of $R^1$ and $R^2$ represents —$CH_2OR^4$ (wherein $R^4$ represents a carboxylic acid residue) while the other one represents alkyl, lower alkyl-substituted or unsubstituted cycloalkyl, aryl, or aralkyl; and
$R^3$ represents —$CH_2OR^5$ (wherein $R^5$ represents a carboxylic residue).

2. A process for producing an alicyclic compound represented by formula (I):

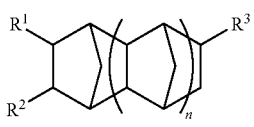

wherein n is an integer of 0 or 1; one of $R^1$ and $R^2$ represents —$CH_2OR^4$ (wherein $R^4$ represents a carboxylic residue) while the other one represents alkyl, lower alkyl-substituted or unsubstituted cycloalkyl, aryl, or aralkyl; and $R^3$ represents —$CH_2OR^5$ (wherein $R^5$ represents a carboxylic residue),
the process comprising subjecting to an esterification reaction with carboxylic acid an alicyclic compound represented by formula (II):

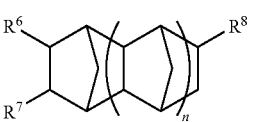

wherein one of $R^6$ and $R^7$ represents hydroxymethyl while the other one represents alkyl, lower alkyl-substituted or unsubstituted cycloalkyl, aryl, or aralkyl; and $R^8$ represents hydroxymethyl.

3. An alicyclic compound represented by formula (II):

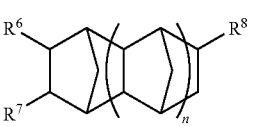

wherein n is an integer of 0 or 1;
one of $R^6$ and $R^7$ represents hydroxymethyl while the other one represents alkyl, lower alkyl-substituted or unsubstituted cycloalkyl, aryl, or aralkyl; and
$R^8$ represents hydroxymethyl.

4. A process for producing an alicyclic compound represented by formula (I):

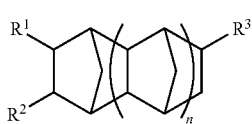

(I)

wherein n is an integer of 0 or 1; one of $R^1$ and $R^2$ represents —$CH_2OR^4$ (wherein $R^4$ represents a carboxylic residue) while the other one represents alkyl, lower alkyl-substituted or unsubstituted cycloalkyl, aryl, or aralkyl; and $R^3$ represents —$CH_2OR^5$ (wherein $R^5$ represents a carboxylic residue)

the process comprising subjecting to a hydrogenation reaction an alicyclic compound represented by formula (IV):

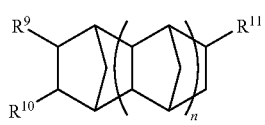

(IV)

wherein one of $R^9$ and $R^{10}$ represents formyl while the other one represents alkyl, lower alkyl-substituted or unsubstituted cycloalkyl, aryl, or aralkyl; and $R^{11}$ represents formyl;

obtaining an alicyclic compound represented by formula (II):

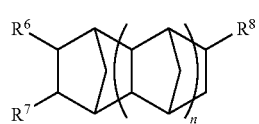

(II)

wherein one of $R^6$ and $R^7$ represents hydroxymethyl while the other one represents alkyl, lower alkyl-substituted or unsubstituted cycloalkyl, aryl, or aralkyl; and $R^8$ represents hydroxymethyl; and subjecting said alicyclic compound according to formula (II) to an esterification reaction with carboxylic acid.

5. An alicyclic compound represented by formula (IV):

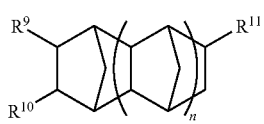

(IV)

wherein n is an integer of 0 or 1;

one of $R^9$ and $R^{10}$ represents formyl while the other one represents alkyl, lower alkyl-substituted or unsubstituted cycloalkyl, aryl, or aralkyl; and $R^{11}$ represents formyl.

* * * * *

UNITED STATES PATENT AND TRADEMARK OFFICE
CERTIFICATE OF CORRECTION

| | |
|---|---|
| PATENT NO. | : 7,902,406 B2 |
| APPLICATION NO. | : 12/066300 |
| DATED | : March 8, 2011 |
| INVENTOR(S) | : Suguru Ohara et al. |

It is certified that error appears in the above-identified patent and that said Letters Patent is hereby corrected as shown below:

COLUMN 1

Line 9, "a" (second occurrence) should read --an--.

COLUMN 3

Line 29, "like can be provided." should read --like.--;
    Line 39, "alkyl" should read --alkyls--;
    Line 40, "alkyl" should read --alkyls--;
    Line 60, "2-methylhexanoic" should read --2-ethylhexanoic--; and
    Line 64, "2,4-dimethylglutaric" should read --2,4-diethylglutaric--.

COLUMN 6

Line 15, "arbitrarily" should be deleted;
    Line 16, "be used." should read --be used arbitrarily.--;
    Line 20, "is" should read --are--;
    Line 25, "water," (second occurrence) should be deleted;
    Line 33, "varies reaction" should read --reaction varies--; and
    Line 60, "an" should read --a--.

COLUMN 7

Line 28, "a" (fourth occurrence) should read --an--; and
    Line 66, "variations" should read --vibrations--.

COLUMN 8

Line 12, "being coexisted" should read --coexisting--.

Signed and Sealed this
Seventeenth Day of May, 2011

David J. Kappos
*Director of the United States Patent and Trademark Office*

CERTIFICATE OF CORRECTION (continued)
U.S. Pat. No. 7,902,406 B2

COLUMN 9

Line 48, "3-methylnorbornene" should read --3-methylnorbornane--; and
    Line 67, "methylnorbornene." should read --methylnorbornane.--.

COLUMN 10

Line 7, "3-methylnorbornene" should read --3-methylnorbornane--.

COLUMN 13

Line 13, "residue)" should read --residue);--.